United States Patent
Jung

(10) Patent No.: US 7,987,661 B2
(45) Date of Patent: Aug. 2, 2011

(54) METHOD FOR DETERMINING MALFUNCTION OF NITROGEN OXIDE SENSOR AND SELECTIVE CATALYTIC REDUCTION SYSTEM OPERATING THE SAME

(75) Inventor: Jae Yoon Jung, Yongin (KR)

(73) Assignees: Hyundai Motor Company, Seoul (KR); Kia Motors Corporation, Seoul (KR)

( * ) Notice: Subject to any disclaimer, the term of this patent is extended or adjusted under 35 U.S.C. 154(b) by 906 days.

(21) Appl. No.: 11/950,772

(22) Filed: Dec. 5, 2007

(65) Prior Publication Data
US 2009/0013666 A1 Jan. 15, 2009

(30) Foreign Application Priority Data
Jul. 9, 2007 (KR) .................. 10-2007-0068795

(51) Int. Cl.
*F01N 3/00* (2006.01)
(52) U.S. Cl. ............... 60/277; 60/285; 60/286; 60/295; 60/301; 60/274
(58) Field of Classification Search .......... 60/277, 60/301, 299, 284–287
See application file for complete search history.

(56) References Cited

U.S. PATENT DOCUMENTS

| | | | | |
|---|---|---|---|---|
| 5,426,934 | A * | 6/1995 | Hunt et al. | 60/276 |
| 6,882,929 | B2 * | 4/2005 | Liang et al. | 701/115 |
| 6,899,093 | B2 * | 5/2005 | Center | 123/681 |
| 7,168,411 | B2 * | 1/2007 | Bourn et al. | 123/396 |
| 7,543,443 | B2 * | 6/2009 | Tsumagari | 60/277 |
| 2006/0218895 | A1 * | 10/2006 | Wickert | 60/277 |
| 2008/0034732 | A1 * | 2/2008 | Hosoya et al. | 60/276 |

* cited by examiner

*Primary Examiner* — Thomas E Denion
*Assistant Examiner* — Jesse Bogue
(74) *Attorney, Agent, or Firm* — Morgan, Lewis & Bockius LLP

(57) ABSTRACT

A method for determining malfunction of a nitrogen oxide sensor compares a nitrogen oxide amount detected by the sensor with a predetermined value of nitrogen oxide. If the difference between the predetermined value and the amount detected by the sensor is within a predetermined range, the method determines whether an engine is in a steady state. If the engine is in a steady state, the method changes one or more engine control parameters, thereby varying an actual nitrogen oxide amount. After changing the parameters, the method determines whether the amount detected by the sensor changes. The method determines that the sensor is malfunctioning if the amount detected by the sensor does not change. A selective catalytic reduction system includes a first nitrogen oxide sensor, a selective catalytic reduction apparatus, and a second nitrogen oxide sensor, all disposed in an exhaust pipe. A control portion performs the above-described method.

8 Claims, 4 Drawing Sheets

METHOD FOR DETERMINING MALFUNCTION OF NITROGEN OXIDE SENSOR AND SELECTIVE CATALYTIC REDUCTION SYSTEM OPERATING THE SAME

CROSS-REFERENCE TO RELATED APPLICATION

This application claims priority to, and the benefit of, Korean Patent Application No. 10-2007-0068795, filed in the Korean Intellectual Property Office on Jul. 9, 2007, the entire contents of which are incorporated herein by reference.

BACKGROUND OF THE INVENTION

1. Field of Invention

The present invention relates to a method for determining malfunction of a nitrogen oxide sensor, and a selective catalytic reduction system.

2. Description of the Related Art

A typical selective catalytic reduction system cleans nitrogen oxide from a factory exhaust pipe by spraying a urea solution onto it. Recent research has addressed applying such a system to vehicle exhaust pipes.

When using such a system, the amount of nitrogen oxide in exhaust gas needs to be measure, usually by mapping or modeling. This poses a problem in vehicles, since the amount of nitrogen oxide changes with driving conditions or other catalyst devices.

To test malfunction of a nitrogen oxide sensor, using only output signals of the sensor is inaccurate. If driving parameters (such as fuel injection amount) are changed at random to test the sensor, noise, power fluctuation, and smoke are generated.

The above information disclosed in this Background section is only for enhancement of understanding of the background of the invention and therefore it may contain information that does not form the prior art that is already known in this country to a person of ordinary skill in the art.

SUMMARY OF THE INVENTION

A method for determining malfunction of a nitrogen oxide sensor compares a nitrogen oxide amount detected by the sensor with a predetermined value of nitrogen oxide. If the difference between the predetermined value and the amount detected by the sensor is within a predetermined range, the method determines whether an engine is in a steady state. If the engine is in a steady state, the method changes one or more engine control parameters, thereby varying an actual nitrogen oxide amount. After changing the parameters, the method determines whether the amount detected by the sensor changes. The method determines that the sensor is malfunctioning if the amount detected by the sensor does not change.

A selective catalytic reduction system for nitrogen oxide of exhaust gas includes an exhaust pipe; a first nitrogen oxide sensor in the exhaust pipe; a selective catalytic reduction apparatus for eliminating the nitrogen oxide, in the exhaust pipe behind the first sensor; a second nitrogen oxide sensor in the exhaust pipe behind the selective catalytic reduction apparatus; and a control portion for determining whether the first sensor is malfunctioning. The control portion performs the above-described method.

The parameters may be pilot injection flux, pilot injection timing, main injection flux, main injection timing, and/or exhaust gas recirculation amount.

Changing the parameters may include determining whether the engine speed is in a middle/low range; if the engine speed is in the middle/low range, determining whether a load, such as an air conditioner, is on or off, and whether a coolant temperature is within a predetermined range; and changing one or more of the parameters based on the coolant temperature and whether the load is on or off. If the engine speed is not in the middle/low speed range, the method may determine whether the load is on or off, and whether the coolant temperature is in the predetermined range; and change a different one or more of the parameters.

Only the main injection timing may be changed, if the coolant temperature is not in the predetermined range, or if the load is on.

DETAILED DESCRIPTION OF PREFERRED EMBODIMENTS

An exemplary embodiment of the present invention will hereinafter be described in detail with reference to the accompanying drawings.

Figure 1:
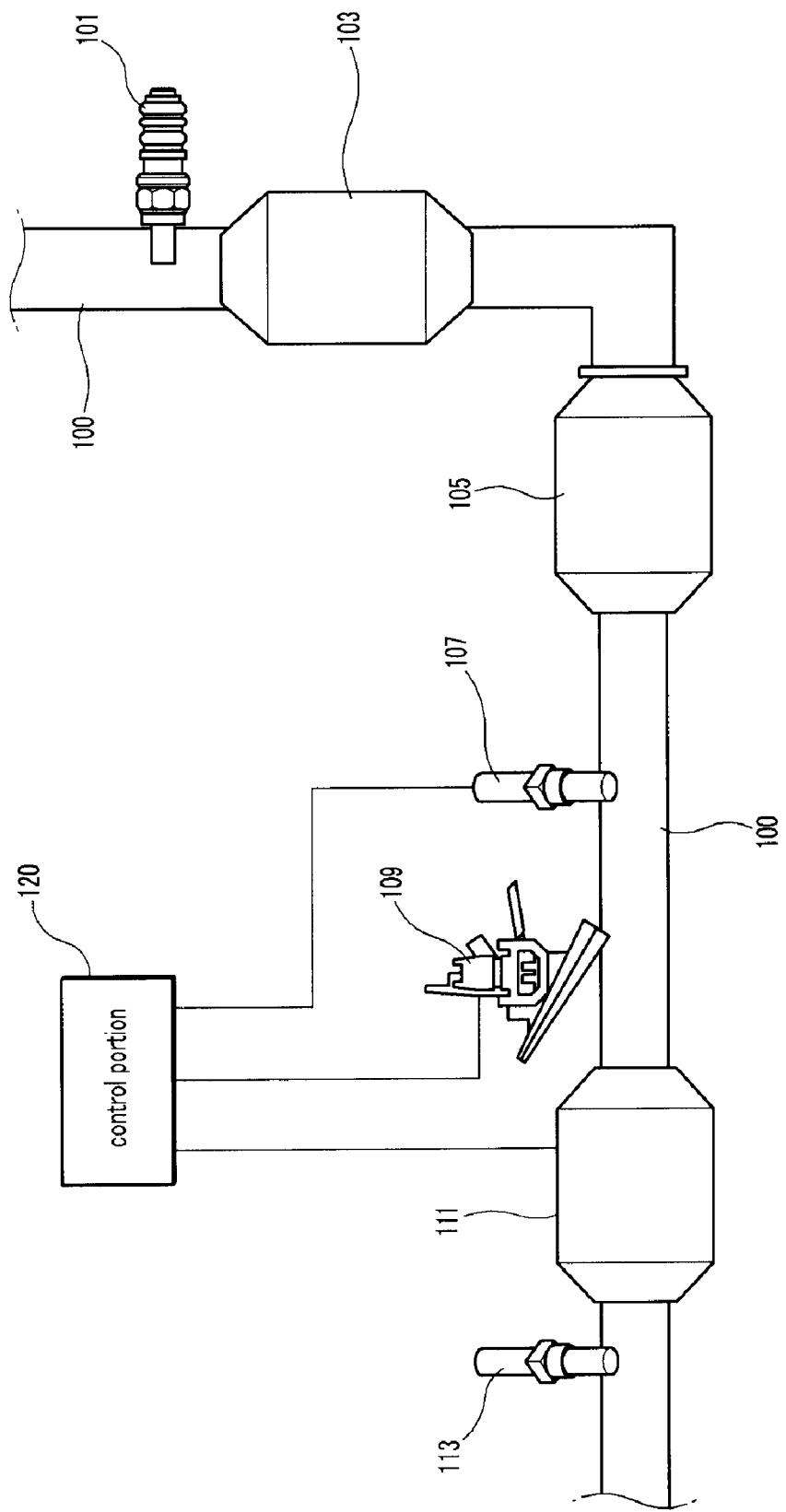
FIG. 1 is a schematic drawing of a selective catalytic system according to an exemplary embodiment of the present invention.

As shown in FIG. 1, a selective catalytic reduction system according to an exemplary embodiment of the present invention includes a wideband oxygen sensor (linear lambda sensor) 101, a first sensor 107, a selective catalytic reduction apparatus 111, a second sensor 113 and a control portion 120.

The wideband oxygen sensor 101 is disposed in an exhaust pipe 100 so as to detect oxygen in exhaust gas, and the first sensor 107 is installed at the rear of the wideband oxygen sensor 101 and detects the nitrogen oxide in the exhaust gas. The selective catalytic apparatus 111 is disposed behind the first sensor 107, and includes a urea injector 109. The second sensor 113 is disposed behind the selective catalytic apparatus and detects nitrogen oxide.

The control portion 120 determines whether the first sensor 107 is disabled or not on the basis of signals from the first sensor 107.

The control portion (engine control unit) 120 includes at least one microprocessor operated by a program that performs the inventive method, which will be described in detail below. The control portion 120 may also include a memory and associated hardware, software, and/or firmware as may be selected and programmed by a person of ordinary skill in the art based on the teachings herein.

In addition, referring to FIG. 1, a diesel oxidation catalyst (DOC) 103, a catalyzed particulate filter (CPF) 105, and other similar elements may be provided to the exhaust pipe 100.

The exhaust gas that is exhausted from an engine (not shown) flows in the exhaust pipe 100 at the top right of FIG. 1, goes through the diesel oxidation catalyst 103 and the catalyzed particulate filter (CPF) 105, and the nitrogen oxide amount is detected by the first sensor 107.

The urea injector 109 injects urea according to the nitrogen oxide amount, and the nitrogen oxide is eliminated in the selective catalyst apparatus 111 by the urea.

Figure 2:
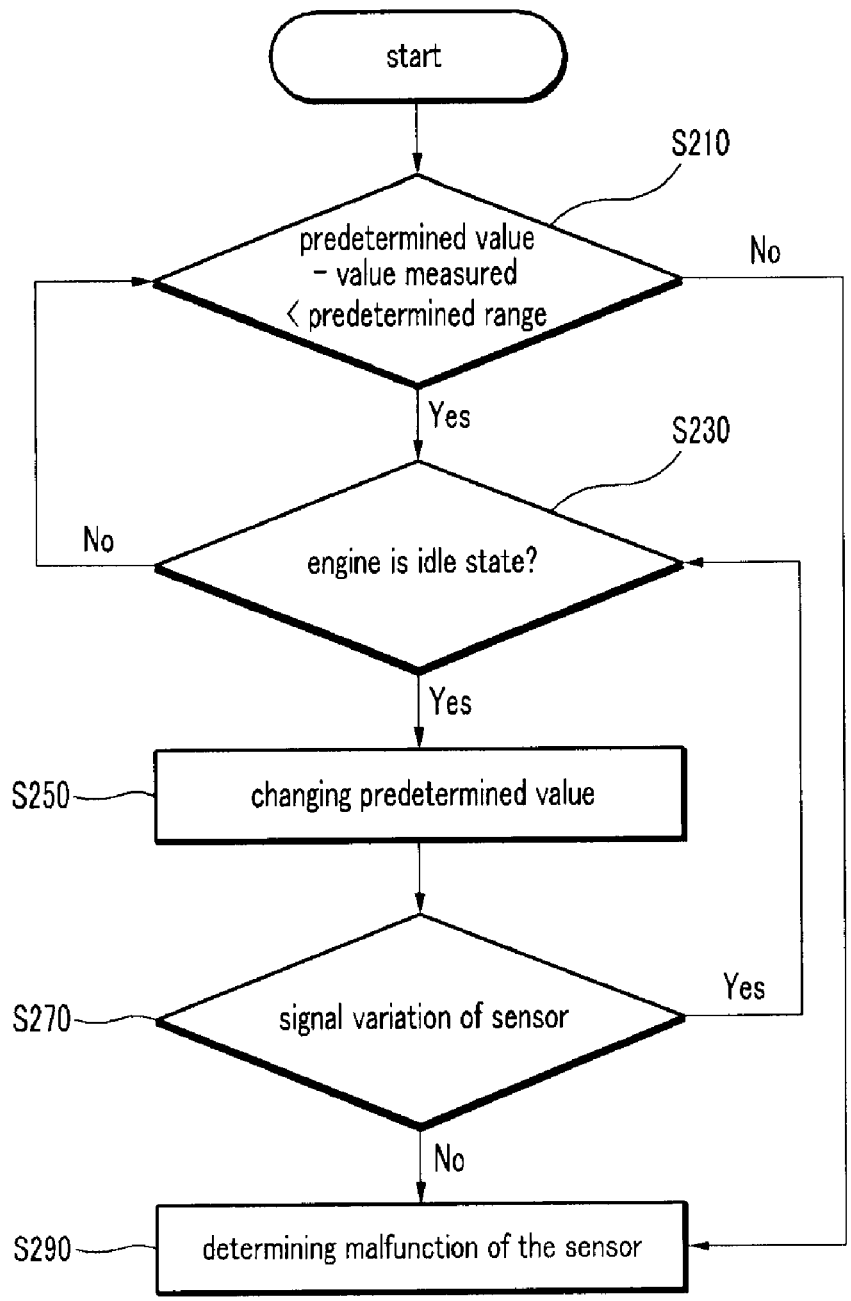
FIGS. 2 and 3 are flowcharts showing a malfunction judgment method of a nitrogen oxide sensor according to an exemplary embodiment of the present invention.
Figure 3:
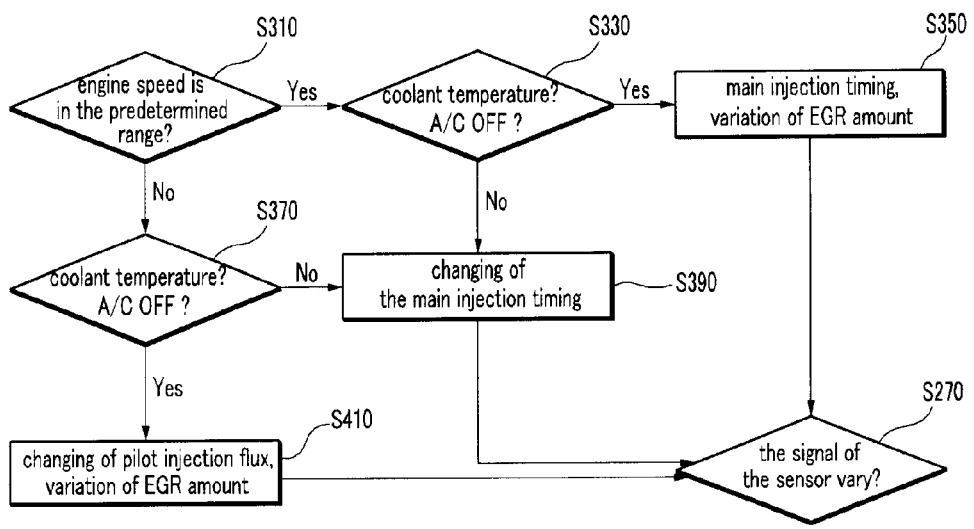

Hereafter, a malfunction judgment method according to an exemplary embodiment of the present invention is explained referring to FIG. 2 and FIG. 3.

Referring to FIG. 2, according to an exemplary embodiment of the present invention, first of all, the control portion 120 compares the nitrogen oxide amount detected by the sensor 107 with a predetermined value of nitrogen oxide corresponding to an engine speed and fuel amount, and determines whether the difference between the actual nitrogen oxide amount and the predetermined value is in a predetermined range (S210).

If the value measured at the first sensor 107 is correct, the selective catalyst apparatus 111 can be controlled correctly. The first sensor 107 is called "sensor" in FIG. 2.

If the difference is in the predetermined range, the control portion 120 determines whether the engine is in a steady state or not (S230). In the steady state, the engine speed and fuel consumption amount are uniform, so malfunction of the sensor 107 is more easily determined in a steady state.

If the engine is determined to be in a steady state (S230), the control portion 120 controls variation of the nitrogen oxide amount by changing engine control parameters (S250), such as pilot injection flux, pilot injection timing, main injection flux, main injection timing, and exhaust gas recirculation amount.

For example, if the pilot injection flux is decreased, the nitrogen oxide amount increases, and if the main injection timing is advanced, the nitrogen oxide amount increases.

When the control parameters are changed, the actual amount of nitrogen oxide changes. Therefore, next, the control portion 120 determines whether the signals of the sensor 107 vary (S270). If the sensor is working correctly, the output value of the sensor 107 varies with the nitrogen oxide amount. If the signals of the sensor 107 do not vary (S290), it is determined that the sensor is malfunctioning.

Hereafter, referring to FIG. 3, step 250 is described in detail.

If the engine is in a steady state (S230), the control portion 120 determines whether the engine speed is in a middle/low speed range (S310), for example, 740 rpm~2500 rpm.

After that, if the engine speed is in the middle/low range, the control portion 120 determines whether an air conditioner is off and whether the coolant temperature is within a predetermined range (S330), such as 25° C.~75° C.

After that, if the coolant temperature is in the predetermined range and the air conditioner is off, the control portion 120 changes the main injection timing and the exhaust gas recirculation amount (S350).

Noise would be caused if the pilot injection flux were changed when the engine speed was high. Therefore, the pilot injection flux and the exhaust gas recirculation amount are changed only if the engine speed is in the middle/low speed range.

The pilot injection amount can be changed, for example, from 1 mm$^3$ to 3 mm$^3$, but the invention is not limited thereto.

If the coolant temperature is above the predetermined range or the air conditioner is on at step S330, the control portion 120 only changes the main injection timing (S390).

When the coolant temperature is over the predetermined temperature or the air conditioner is on, the idle state may be unstable, or smoke may be caused, so the control portion 120 only changes the main injection timing to avoid side effects.

In some embodiments, the control portion 120 only changes the main injection timing if other apparatuses such as a heater, alternator, fan, power steering, or power window are operating.

After step S350 or S390 is performed (S270), the method determines whether the sensor signal varies, as described above.

If the engine speed is not in the middle/low speed range at step S310, if the coolant temperature is in the predetermined range, and if the air conditioner is off (S370), as mentioned above, the idle state may be unstable or smoke may result from a change of the exhaust gas recirculation amount.

Therefore, in step S410, the control portion 120 changes the pilot injection flux and the exhaust gas recirculation amount if the coolant temperature is in the predetermined range and the air conditioner is off.

That is, because at this time the engine is determined to be operating at a high speed in step S310, if the main injection timing were changed, output of the engine would also change.

If the coolant temperature is above the predetermined range or the air conditioner is on, in step S370 the control portion 120 only changes the main injection timing (S390), because the idle state can be unstable or smoke can be caused.

In some embodiments, the control portion 120 only changes the main injection timing if other apparatuses apply a load to the engine, such as a heater, alternator, fan, power steering, or power windows.

The change the main injection timing, the crank angle can be moved forward or backward by ~10 degrees in a manner that can be implemented by a person of ordinary skill in the art based on the teachings herein.

After step S410 occurs, the control portion 120 determines whether the sensor signal varies (S270).

Alternatively, the control portion 120 can diagnose malfunction of the sensor on the basis of the output value of the sensor 107.

Figure 4:
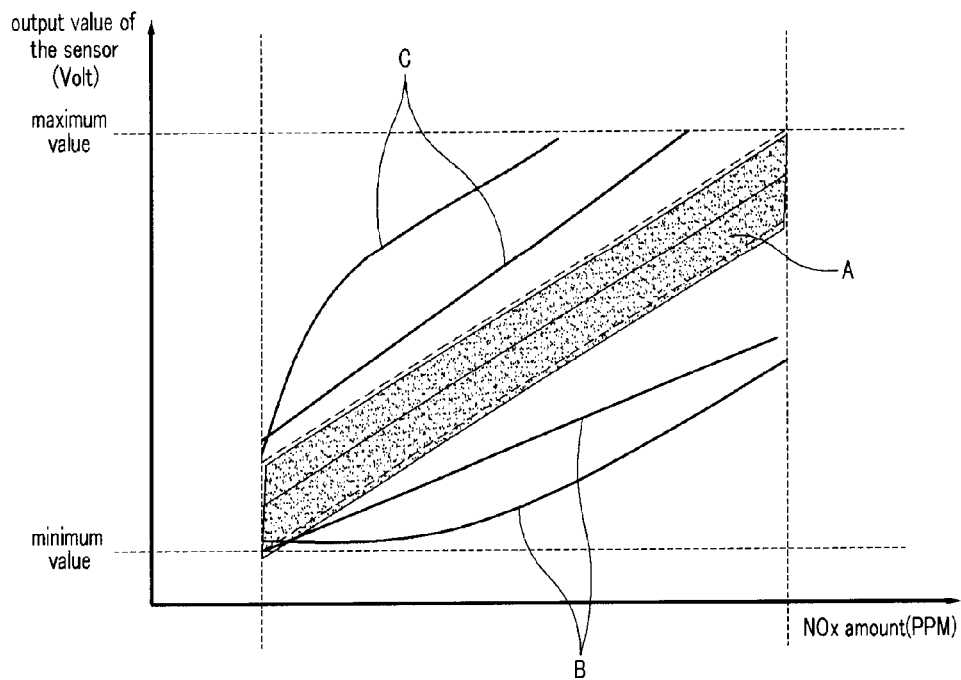
FIG. 4 is a graph showing an output range of the nitrogen oxide sensor according to an exemplary embodiment of the present invention.
Figure 5:
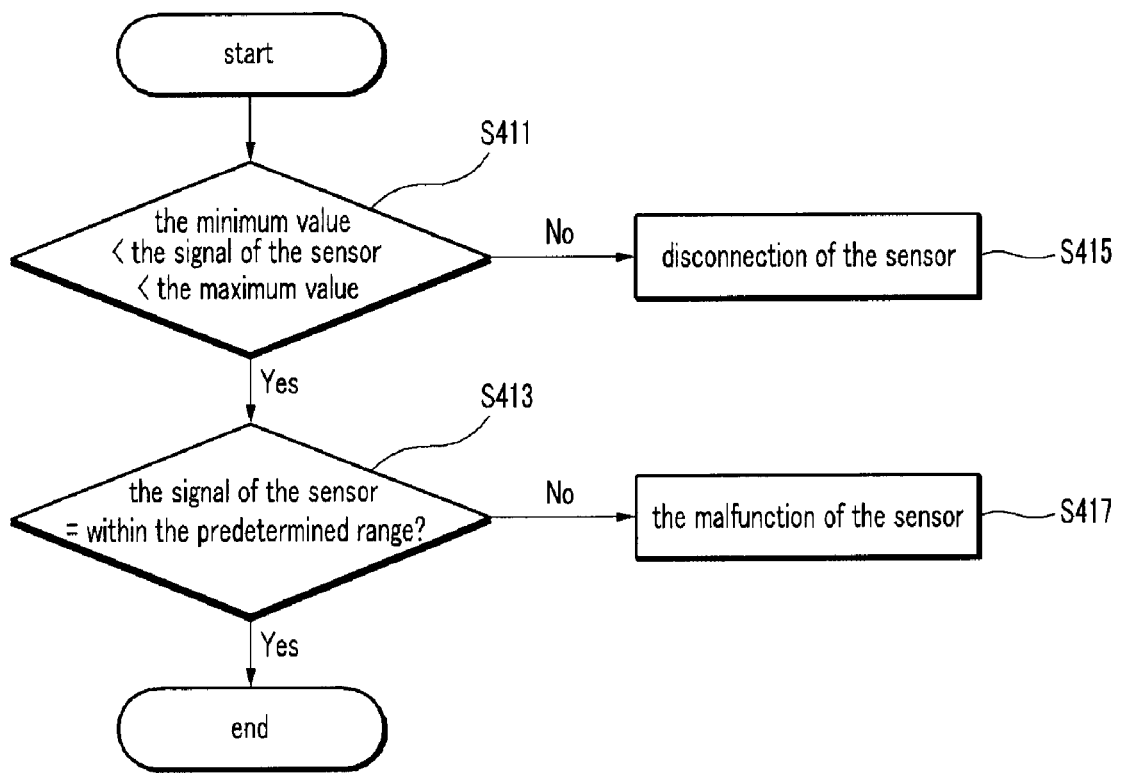
FIG. 5 is a flowchart showing the malfunction judgment method of the sensor on the basis of an output value of the nitrogen oxide sensor according to an exemplary embodiment of the present invention.

FIG. 4 is a graph showing an output range of the nitrogen oxide sensor according to an exemplary embodiment of the present invention, and FIG. 5 is a drawing showing the malfunction judgment method of the sensor on the basis of output value of the sensor according to an exemplary embodiment of the present invention.

Referring to FIG. 4, output values of the sensor 107 within the "A" range are indicative of a normally functioning sensor.

However, if the output value of the sensor 107 is within the range "B" or "C" and the output value is between the maximum and minimum output values shown in FIG. 4, the control portion 120 determines that the sensor 107 is malfunctioning.

In more detail, referring to FIG. 5, the control portion 120 determines whether the signal of the sensor 107 is between the predetermined maximum value and minimum value or not (S411). The maximum and minimum values can be selected by a person of ordinary skill in the art based on the kind of the sensor 107 being used.

Then, the control portion 120 determines whether the signal of the sensor is within a predetermined range or not (S413) if the signal of the sensor 107 is between the maximum value and the minimum value. That is, the control portion 120 determines whether the output value of the sensor 107 is in a range that the sensor 107 can generate, on the basis of the map data.

If the signal of the sensor 107 is not within the predetermined range, the control sensor 107 determines that the sensor 107 is malfunctioning (S417).

If the signal outputted from the sensor 107 is greater than the maximum value or less than the minimum value in step S411, the control portion 120 determines that the sensor 107 has a disconnected portion or a short circuit (S415).

The steps from S411 to S417 can be operated earlier than step S210.

According to exemplary embodiments of the present invention, a nitrogen oxide sensor can be diagnosed without noise, change of engine output, unstable states of the engine, or smoke.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and range of the appended claims.

What is claimed is:

1. A method for determining malfunction of a nitrogen oxide sensor, comprising:
   comparing a nitrogen oxide amount detected by the sensor with a predetermined value of nitrogen oxide;
   if a difference between the predetermined value and the amount detected by the sensor is within a predetermined range, determining whether an engine is in a steady state;
   if the engine is in a steady state, changing one or more engine control parameters, thereby varying an actual nitrogen oxide amount;
   after changing the parameters, determining whether the amount detected by the sensor changes; and
   determining a malfunction of the sensor if the amount detected by the sensor does not change;
   wherein the parameters comprise at least one member selected from the group consisting of pilot injection flux, pilot injection timing, main injection flux, main injection timing, exhaust gas recirculation amount, and combinations thereof; and
   wherein changing the parameters comprises:
      determining whether an engine speed is in a middle/low range;
      if the engine speed is in the middle/low range, determining whether a load is on or off, and whether a coolant temperature is within a predetermined range; and
      changing one or more of the parameters based on the coolant temperature and whether the load is on or off.

2. The method of claim 1, wherein the load comprises an air conditioner.

3. The method of claim 1, further comprising, if the engine speed is not in the middle/low speed range:
   determining whether the load is on or off, and whether the coolant temperature is in the predetermined range; and
   changing a different one or more of the parameters.

4. The method of claim 1, further comprising changing only the main injection timing, if the coolant temperature is not in the predetermined range or the load is on.

5. A selective catalytic reduction system for nitrogen oxide of exhaust gas, comprising:
   an exhaust pipe;
   a first nitrogen oxide sensor disposed in the exhaust pipe;
   a selective catalytic reduction apparatus for eliminating the nitrogen oxide, disposed in the exhaust pipe behind the first sensor;
   a second nitrogen oxide sensor disposed in the exhaust pipe behind the selective catalytic reduction apparatus; and
   a control portion for determining whether the first sensor is malfunctioning, wherein the control portion performs:
      comparing a nitrogen oxide amount detected by the first sensor with a predetermined value;
      if a difference between the predetermined value and the amount detected by the first sensor is in a predetermined range, determining whether an engine is in a steady state;
      if the engine is in a steady state, changing at least one engine control parameter, thereby changing an actual nitrogen oxide amount;
      after changing the parameter, determining whether the amount detected by the first sensor changes; and
      determining a malfunction of the first sensor in a case if the amount does not change;
   wherein the parameters comprise at least one member selected from the group consisting of pilot injection flux, pilot injection timing, main injection flux, main injection timing, exhaust gas recirculation amount, and combinations thereof; and
   wherein changing the parameters comprises:
      determining whether an engine speed is in a middle/low range;
      if the engine speed is in the middle/low range, determining whether a load is on or off, and whether a coolant temperature is within a predetermined range; and
      changing one or more of the parameters based on the coolant temperature and whether the load is on or off.

6. The system of claim 5, wherein the load comprises an air conditioner.

7. The system of claim 5, further comprising, if the engine speed is not in the middle/low speed range:
   determining whether the load is on or off, and whether the coolant temperature is in the predetermined range; and
   changing a different one or more of the parameters.

8. The system of claim 5, further comprising changing only the main injection timing, if the coolant temperature is not in the predetermined range or the load is on.

* * * * *